United States Patent [19]

Ito et al.

[11] Patent Number: 5,436,166
[45] Date of Patent: Jul. 25, 1995

[54] METHOD OF AND APPARATUS FOR PERFORMING CHROMATOGRAPHY ANALYSIS OF UNKNOWN SAMPLE

[75] Inventors: Masahito Ito; Junkichi Miura; Yoshio Fujii; Hiroshi Satake; Fuzio Yamada, all of Katsuta; Kouichi Tagami; Fuminori Umesato, both of Ibaraki, all of Japan

[73] Assignee: Hitachi, Ltd., Tokyo, Japan

[21] Appl. No.: 180,472

[22] Filed: Jan. 12, 1994

Related U.S. Application Data

[63] Continuation of Ser. No. 836,599, Feb. 18, 1992, abandoned.

[30] Foreign Application Priority Data

Feb. 18, 1991 [JP] Japan .................................. 3-023127

[51] Int. Cl.6 ............................................. B01D 15/08
[52] U.S. Cl. ................................... 436/161; 73/23.36; 73/61.57; 95/82; 96/102; 96/103; 210/198.2; 210/656; 422/70; 422/89
[58] Field of Search ..................... 436/161; 422/70, 89; 73/23.21, 23.22, 23.36, 61.57, 61.52; 210/656, 198.2; 96/101, 102, 103; 95/82

[56] References Cited

U.S. PATENT DOCUMENTS

| 3,898,837 | 8/1975 | Boege ................... 73/23.36 |
| 4,006,624 | 2/1977 | Annino et al. . | |
| 4,180,857 | 12/1979 | Yoshihara et al. ............. 364/497 |
| 4,266,277 | 5/1981 | Issenmann .................. 73/23.36 |
| 4,353,242 | 10/1982 | Harris et al. ................ 73/23.36 |
| 4,592,842 | 6/1986 | Tomlinson ................. 210/659 |
| 4,740,903 | 4/1988 | Nakatsuka et al. ............ 364/497 |
| 4,807,148 | 2/1989 | Lacey ..................... 73/23.36 |
| 4,837,726 | 6/1989 | Hunkapiller ................. 364/497 |
| 4,941,101 | 7/1990 | Crilly ...................... 364/497 |
| 5,119,315 | 6/1992 | Kemp et al. ................. 364/498 |

FOREIGN PATENT DOCUMENTS

| 60-239669 | 11/1985 | Japan . |
| 63-290958 | 11/1988 | Japan . |
| 0191055 | 8/1989 | Japan . |
| 1244360 | 9/1989 | Japan . |
| 0196959 | 8/1990 | Japan . |
| 2196959 | 8/1990 | Japan . |
| 0105248 | 5/1991 | Japan . |
| 0156367 | 7/1991 | Japan . |

OTHER PUBLICATIONS

Patent Abstracts of Japan vol. 14 No. 484 Oct. 22, 1990. Abstract of 02-196959.

Primary Examiner—James C. Housel
Assistant Examiner—Jan M. Ludlow
Attorney, Agent, or Firm—Antonelli, Terry, Stout & Kraus

[57] ABSTRACT

The present invention relates to a chromatography analysis method and a system employing the same which are capable of automatically determining an constituents to be detected contained in the unknown sample based on results on measuring a standard sample. The standard sample is first separated to obtain its chromatogram. The system extracts the necessary information from the chromatogram to identify the peaks corresponding to the constituents to be detected to set widths of time windows for the peaks. Then, the time windows thus set are applied to the chromatograms obtained by the separation of the unknown sample to identify the constituents contained in the unknown sample. By employing the present invention, it is unnecessary for an operator to input the retention time of each constituent to the system.

10 Claims, 8 Drawing Sheets

METHOD OF AND APPARATUS FOR PERFORMING CHROMATOGRAPHY ANALYSIS OF UNKNOWN SAMPLE

RELATED APPLICATION

This application is a continuation of application Ser. No. 836,599 filed on Feb. 18, 1992, now abandoned. U.S. application Ser. No. 149,701 filed on Nov. 9, 1993, which is a continuation of U.S. application Ser. No. 763,203 filed on Sep. 20, 1991, now abandoned, is related to the present application, and subject matter from that application is included in the present specification.

BACKGROUND OF THE INVENTION

The present invention relates to a method of making a chromatography analysis of samples and a system employing the same, and more particularly to a method of using an analyzer including a chromatograph having a separation column and a detector, and a sampler for automatically introducing samples into the chromatograph, and a system employing same.

In general, when an analyzer is used, analytical conditions are determined by an analyst and are set by inputting numeric values and the like from a keyboard and by adjusting a variable resistor. Especially in the case where a plurality of constituents are analyzed, the analytic conditions for identifying the individual constituents first must be set. For example, a retention time and its tolerance in identification of constituents by a chromatograph are judged on the basis of the measurement results of preparatory samples by an analyst and are then inputted into a data processing unit. With JP-A-63-290958 as which is directed to peak tracking, the retention times of the peaks on a chromatogram as the reference are inputted by an analyst.

Further, in JP-A-60-239669, the conversion of the time base from one chromatogram to another chromatogram is performed with the main peaks being used as the reference between the two chromatograms. This is available as a method of identifying a peak between the chromatograms in which the retention times are changed, but the retention times of the peaks on the chromatogram as the reference are also judged by the operator.

Furthermore, in the prior art such as the above-mentioned JP-A-63-290958 and JP-A-60-239669, prior to the analysis of the unknown samples, the operator always needed to set the analytic conditions once.

SUMMARY OF THE INVENTION

It is therefore an object of the present invention to provide a method of making a chromatography analysis of samples and a system employing the same in which an analyzer itself is capable of automatically determining constituents to be detected contained in the samples.

It is another object of the present invention to provide a method of making a chromatography analysis of samples and a system employing the same in which an operator does not need to input retention times of the individual constituents to be analyzed into an analyzer.

The present invention may provide the steps of:
introducing a known sample such as a standard sample into a chromatograph by actuating a sampler capable of introducing a sample into the chromatograph on the basis of an operation start signal to obtain a chromatogram of the known sample;

obtaining a peak corresponding to a constituent to be measured on the basis of the chromatogram of the known sample to set a width of a time window of the peak;

introducing an unknown sample into the chromatograph to obtain a chromatogram of the unknown sample; and applying the set time window to the chromatogram of the unknown sample to identify a constituent contained in the unknown sample.

In a preferred embodiment of the present invention, there are carried out the steps of:

paying attention to one or more peaks existing in a time window with a large width applied to a chromatogram of a known sample to determine that the one or more peaks are peaks corresponding to constituents to be measured based on the condition that areas and heights of the individual peaks conform to the constituents to be measured; and setting individual time windows each having a small width to the peaks which are employed after a relationship between the constituents and the peaks has been established.

DESCRIPTION OF THE PREFERRED EMBODIMENTS

In the present invention, a chromatogram obtained as the measurement result of a known sample such as a standard sample is utilized to determine retention times of constituents to be detected contained in a series of unknown samples.

First, the information for qualitative and quantitative analyses are extracted from the measurement result of the standard sample. Then, it is judged whether or not this information is sufficient. If the information is insufficient, the analytic conditions for the control are reexamined and the measurement of the standard sample is continued until the information becomes sufficient. On the other hand, if the information is sufficient, the reference for the qualitative and quantitative analyses are expressed by some values to determine the analytic conditions for identification, data analysis and the like.

In order to carry out the present invention, predetermined components constituting the analyzer and predetermined reagents are used. In the case of a chromatograph system, a column, an eluent and the standard sample correspond to those components and reagents. The component and the reagent are not necessarily one pair. That is, a plurality of combinations may be available as long as the analyzer can recognize the pair of interest of the combinations.

The first embodiment of the present invention will hereinafter be described with reference to FIGS. 1-3 and 4A-4C.

Figure 1:
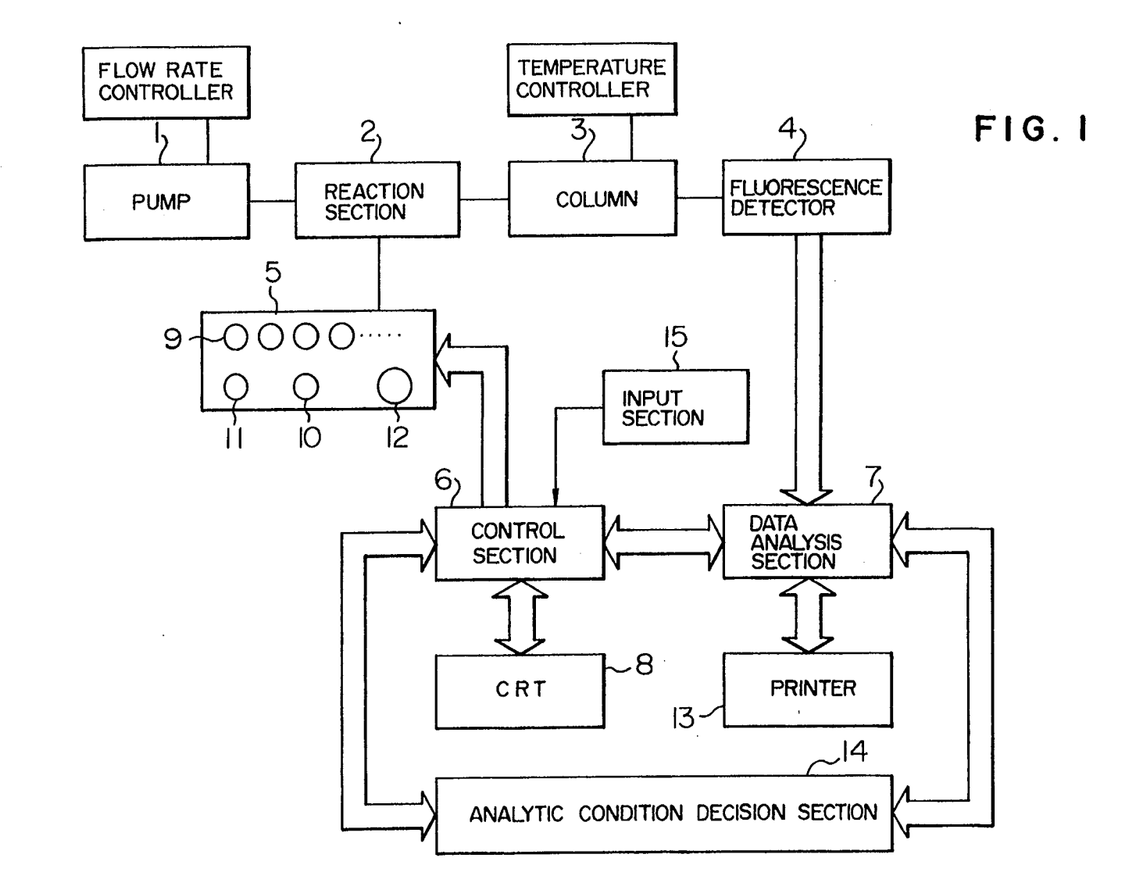
FIG. 1 is a block diagram showing a system arrangement of a catecholamine analyzer as a first embodiment of the present invention.

FIG. 1 is a block diagram showing a system arrangement of a liquid chromatograph system for analyzing catecholamine to which the present invention is applied. With this analyzer, before separating catecholamine, the catecholamine is pre-derivatized with a fluorescence label and then is absorbed in a pre-column provided in a reaction section once to eliminate impurities, and thereafter is introduced as a sample into a separation column. To a mechanism control section 6 is connected an input section 15 provided with a start key. An autosampler 5 is provided with a movable pipetting nozzle 38. In this connection, the needle 38 is movable so as to be positionable in a container 10 having a fluorescent derivatizing reagent solution put thereinto, a standard sample container 11, a mixing chamber 12 and unknown sample containers 9.

When an operator for the analyzer presses the start key provided in the input section 15 of the analyzer, the autosampler 5 sucks in 400 μl of the standard sample to eject it into the mixing chamber 12 in response to an instruction from the mechanism control section 6. In the standard sample in container 11 are contained three kinds of catecholamine, i.e., 1,000 pg/ml of norepinephrine (NE), 1,000 pg/ml of epinephrine (E) and 1,000 pg/ml of dopamine (DA). Subsequently, an aqueous solution in container 10 of a fluorescent derivatizing reagent consisting of 400 μl of 60 mM of 1,2-diphenylethylenediamine (DPE) is sucked to be ejected to the mixing chamber 12 to be mixed with the standard sample in container 11. 400 μl of the resultant mixed liquid is fed to a measuring pipe 64 in a reaction section 2 to derive the fluorescent derivatizing reaction.

After the elapse of three minutes, the derivatized catecholamine is once absorbed in a pre-column 65 in the reaction section 2. After the elapse of another three minutes, the derivatized catecholamine is fed together with an eluent, which is fed from an eluent feeding pump 1 by valve switching, to the separation column 3 to be separated and spread by reversed phase chromatography. Finally, it is detected by a fluorescence detector 4. The chromatogram as the detected data is stored in a data analysis section 7.

Figure 2:
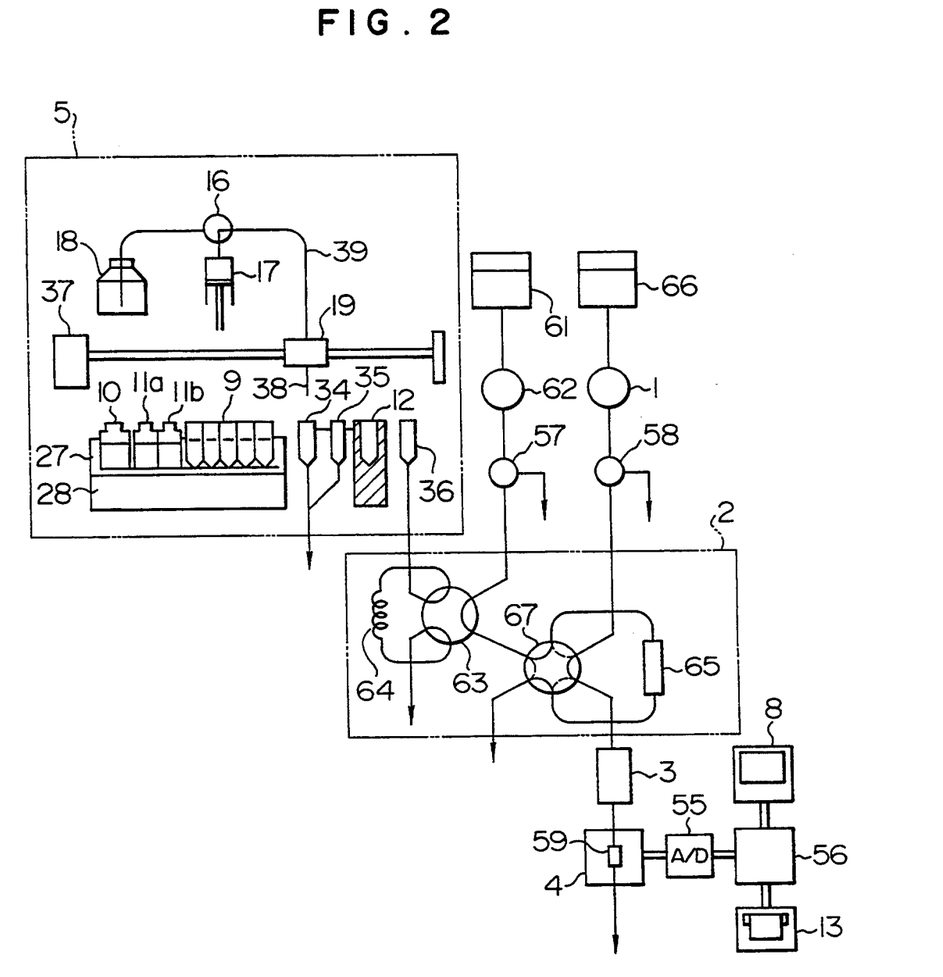
FIG. 2 is a view, partially diagram, partially block diagram, useful in explaining a flow line system in the system of FIG. 1.

The flow line system in the system of FIG. 1 will now be described referring to FIG. 2.

A detachable sample rack 27 is mounted on a stage 28 in the autosampler 5 of the catecholamine analyzer. The sample rack 27 holds a plurality of sample containers 9 having blood plasma samples put thereinto. Moreover, in the sample rack 27, the reaction reagent container 10 for the fluorescent derivatizing, and standard sample containers 11a and 11b are disposed. In this autosampler 5, the mixing chamber 12, a nozzle cleaning vessel 34, a drain port 35 and an injection port 36 are provided in fixed positions near the stage 28.

The pipetting nozzle 38 serves to pipet the sample or reagent into the mixing chamber 12 by pipetting, or transfer the mixed sample from the mixing chamber 12 to the injection port 36. A drive mechanism 37 has X-, Y- and Z-drive functions so that it can drive the pipetting nozzle 38 in the length, breadth or vertical direction freely to move the nozzle 38 to the position over any container or port in the sampler. The upper end of the pipetting nozzle 38 is coupled through a three-way valve 16 to a pipetting pump 17 and a cleaning liquid vessel 18 by a capillary 39 such as a plastic tube. A holding portion 19 for holding the pipetting nozzle 38 is capable of moving on a rail. The pipetting pump 17 is a pump of cylinder type which is driven by a pulse motor.

In the flow line system having a pre-column 65, a cleaning liquid from a liquid vessel 61 is fed through a sample introducing valve 63 to the pre-column 65 at a fixed flow rate by a pump 62. A measuring pipe 64, which is additionally provided in the sample introducing valve 63, measures the sample mixed liquid injected from the injection port 36.

The eluent from an eluent vessel 66 is fed to the separation column 3 at a fixed flow rate by a pump 1. In this connection, this eluent is fed through a column switching valve 67 to the separation column 3. By changing over the column switching valve 67, the eluent is fed via the pre-column 65. In this regard, the sample which has been processed in the pre-column 65 is fed to the separation column 3.

The sample constituents which have been eluted from the separation column 3 flow through a flow cell 59 of fluorescence detector 4. The measuring signal obtained by the fluorophotometer 4 is inputted through an analog-to-digital converter 55 to a signal processing unit 56. The signal processing unit 56 includes the data analysis section 7 and the analytic condition decision section 14 shown in FIG. 1 and is capable of outputting the result of the signal processing to a printer 13 and a CRT 8. Switching valves 57 and 58 are provided in such a way as to be able to purge the liquid in the pumps 62 and 1 as required.

Next, the description will be given to the method of identifying the constituent to be analyzed on the basis of the chromatogram of the standard sample with reference to FIG. 3. This identification method is a method wherein the width of the time window as the identification tolerance is limited on the basis of the chromatogram of the standard sample 11. Then, this method is referred to as a reduced window method when applicable. This method utilizes the fact that the peaks of the three catecholamine constituents contained in the standard sample 11 where detected are much larger than those based on impurities. The data analysis section 7 first applies the time windows listed in Table 1 to the chromatogram 20 and identifies three peaks 23, 22 and 21 as DA, E and NE, respectively, in the order of decreasing retention time. In the case where a plurality of peaks are present in one time window, the peak having a larger retention time is identified.

TABLE 1

|  | Retention time (min) | ± Tolerance (min) |
| --- | --- | --- |
| NE | 1.00 | 0.30 |
| E | 1.50 | 0.50 |
| DA | 2.50 | 1.00 |

The data analysis section 7 transfers the information of the retention time $t_R$, the peak area A and the peak height h relating to the peaks 21, 22 and 23 obtained from the chromatogram 20 to the analytic condition decision section 14. The section 14 judges whether or not the information relating to those peaks conforms to the conditions listed in Table 2. Then, if so, the section 14 issues an instruction to the data analysis section 7 so as to reduce the width of the time window. Then, the time windows each having a small width corresponding to the peaks 21, 22 and 23, respectively, are set. The center of each time window having a small width is the retention time of each peak. The tolerance from a reduced center is, as shown in Table 3, a small time width. This results in a reduced error in identification when such reduced time windows are applied to the chromatograms of the unknown samples. When the data analysis section 7 analyzes the chromatogram 20, a predetermined threshold is applied to the peak height. Then, in the case where three peaks exceeding the threshold cannot be obtained in the chromatogram 20, the identification is judged to be an error.

Figure 4A:
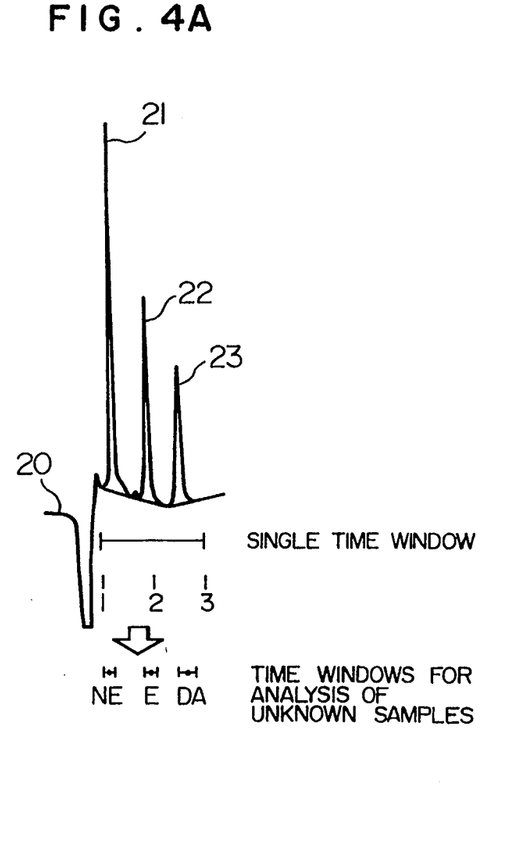
FIG. 4A is a view useful in explaining another peak identification method.
Figure 4B:
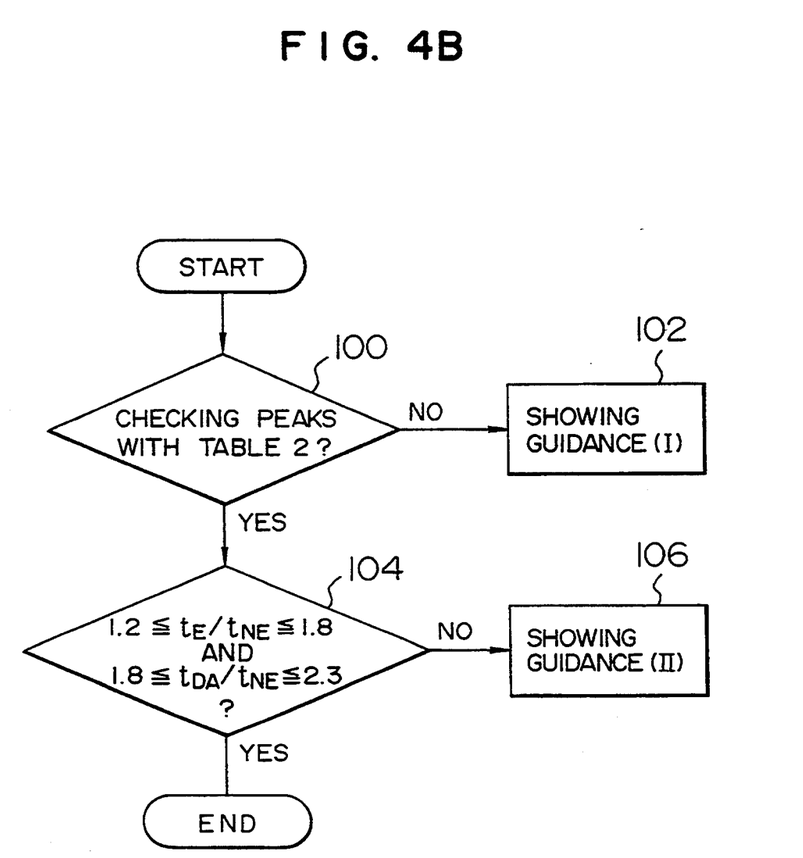
FIG. 4B is a flow-chart of another embodiment.

FIG. 4B shows another embodiment. In step (100), each peak is checked against the conditions listed in Table 2. If any one of the peaks does not conform to the conditions, guidance (I) is shown on CRT 8 as follows (step 102).

"Peak(s) out of normal range. Please check column and reagents."

On the other hand, if all of the peaks conform to the conditions, the correlation among the peaks are judged in step (104). The correlation is indicated by the ratio of retention times of the peaks and the ratio denotes the balance of the respective retention times. If the ratio is out of the conditions listed in step (102), guidance (II) is shown on CRT 8 as follows (step 104).

"Balance of respective retention times of peaks is abnormal. Please check column and reagents"

Incidentally, the balance among the retention times may be judged by calculating differences thereof. In this case, the conditions listed in step (104) are replaced by the following conditions:

$$t_E - t_{NE} < 0.30 \text{ min.}$$

and $$t_{DA} - t_E < 0.60 \text{ min.}$$

When the unknown sample introduced into the chromatograph by the autosampler 5 is separated into constituents and the measurement result is obtained in the form of the chromatogram, a individual time windows each having a small width listed in Table 3 are applied to the chromatogram of the unknown sample so that the constituents contained in the unknown sample are identified.

TABLE 2

|    | Amin ($\mu V \cdot s$) | Amax ($\mu V \cdot s$) | (A/h) max (s) |
|----|------------------------|------------------------|---------------|
| NE | 200,000                | 2,000,000              | 10.0          |
| E  | 150,000                | 1,500,000              | 20.0          |
| DA | 100,000                | 1,000,000              | 30.0          |

TABLE 3

|    | Retention time (min) | ± Tolerance (min) |
|----|----------------------|-------------------|
| NE | 1.22                 | 0.10              |
| E  | 1.89                 | 0.10              |
| DA | 2.55                 | 0.20              |

Next, another peak identification method will be described referring to FIG. 4A. This identification method is a method wherein a single time window is first applied to the chromatogram of the standard sample to identify the peaks of a plurality of constituents to be detected.

The data analysis section 7 counts the peaks in the chromatogram 20 appearing in the single time window and having areas more than or equal to 100,000 $\mu V \cdot S$. Only if three such peaks are present does the section 7 transfer the retention time $t_R$, the peak area A and the peak height h to the analytic condition decision section 14. Otherwise, the identification is judged to be an error. The single time window may cover the whole area of the chromatogram. The analytic condition decision section 14 diagnoses the measurement result on the basis of Table 2 in the same manner as described above. If the measurement result is acceptable, the section 14 issues an instruction to the data analysis section 7 to use the reduced time windows of Table 3 for the analysis of the unknown samples.

Figure 3:
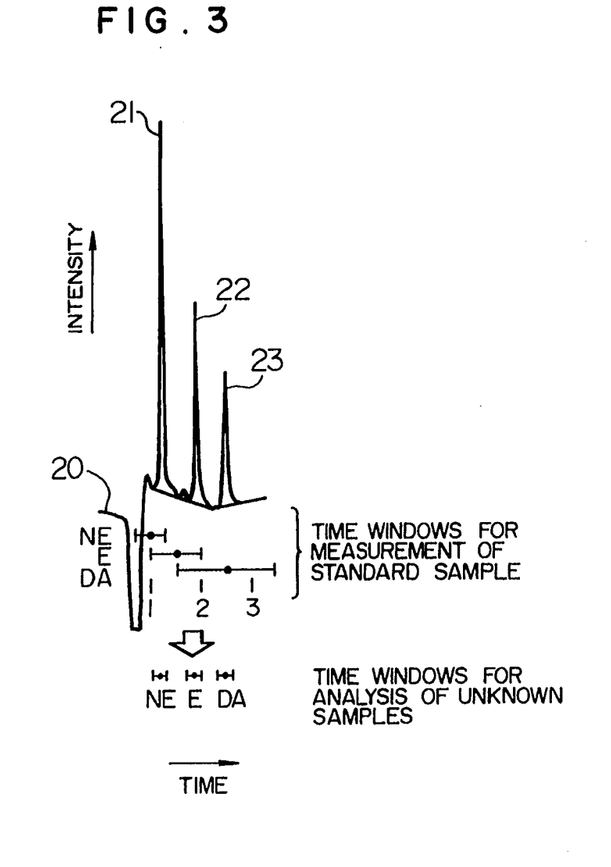
FIG. 3 is a view useful in explaining a peak identification method employed in the system of FIG. 1.

The time windows of Table 3 which are automatically determined on the basis of the method of FIG. 3 or FIG. 4A are overwritten on the chromatogram 20 by the printer 13. Moreover, those time windows may be displayed on the chromatogram on the CRT 8. Thereafter, in the analysis of the unknown sample 9 such as blood plasma, those time windows are used to analyze the data. The quantitative analysis of the unknown sample is performed by the proportional calculation using the peak areas of the standard sample as the reference. More specifically, the area of each peak of each constituent which is identified on the basis of the individual time windows of Table 3 is compared with the area of each peak of the standard sample. Then, the concentration of each constituent of the unknown sample is proportionally calculated based on the condition that the peak area of each constituent of the standard sample is 1,000 pg/ml.

During the operation of the analysis, an error may occur in some cases. Some causes may be considered for such an error. In the case where the column, reagent or component is degraded, the analyst is informed of this information so that the exchange of the degraded column, reagent or component is required. In addition thereto, there may be a case where the analyzer itself changes the control conditions so that the analysis can be carried out without any hindrance. For example, when the peaks are generally small, it is practicable to increase the amplification factor of the fluorescence detector 4, raise the reaction temperature of the reaction section 2, or extend the reaction time thereof. Moreover, when the retention times of the peaks are short, it is practicable to decrease the flow rate of the pump 1 or reduce the temperature of the column 3. When the error occurs, the analytic condition decision section 14 orders the mechanism control section 6 to change the control conditions of the individual drive sections, using the rules established on the basis of the data from the chromatogram 20 and the sensors. For example, in the case where the retention time of the final peak is longer than that of the reference, first, the margin of the separation of each peak is evaluated on the basis of the resolution Rs, the interval of the retention time $\Delta T_R$ and the theoretical plate number N. If the margin of separation is large enough and the pressure is less than the reference value, the calculation is performed in such a way that the retention time of the final peak is within the reference value, thus increasing the flow rate of the pump 1. Even when the margin of separation is large enough, if the pressure is more than or equal to the reference value, the calculation is performed in accordance with the rules and it is simultaneously ordered to raise the temperature of the column 3 and increase the flow rate of the pump 1. The mechanism control section 6 changes the conditions of the control in such a manner as described above and controls the operation of each drive section in such a way that the standard sample 11 is again measured.

Moreover, for the purpose of measuring the state of the reaction, there is proposed a method wherein two samples having known concentrations are used. More specifically, a standard sample 11a containing 1,000 pg/ml of NE, 1,000 pg/ml of E and 1,000 pg/ml of DA, and a standard sample 11b containing 500 pg/ml of NE, 1,000 pg/ml of E and 2,000 pg/ml of DA are individually measured. If the linearity of the reaction is normal, the measurement result of the sample 11b has a determination value which is proportional to the concentration. If the linearity of the reaction is less than or equal to the reference, the analytic condition decision section 14 performs the calculation in accordance with a predetermined rules and orders the mechanism control section 6 to reset the conditions of the reaction temperature and the reaction time of the reaction section 2.

Figure 4C:
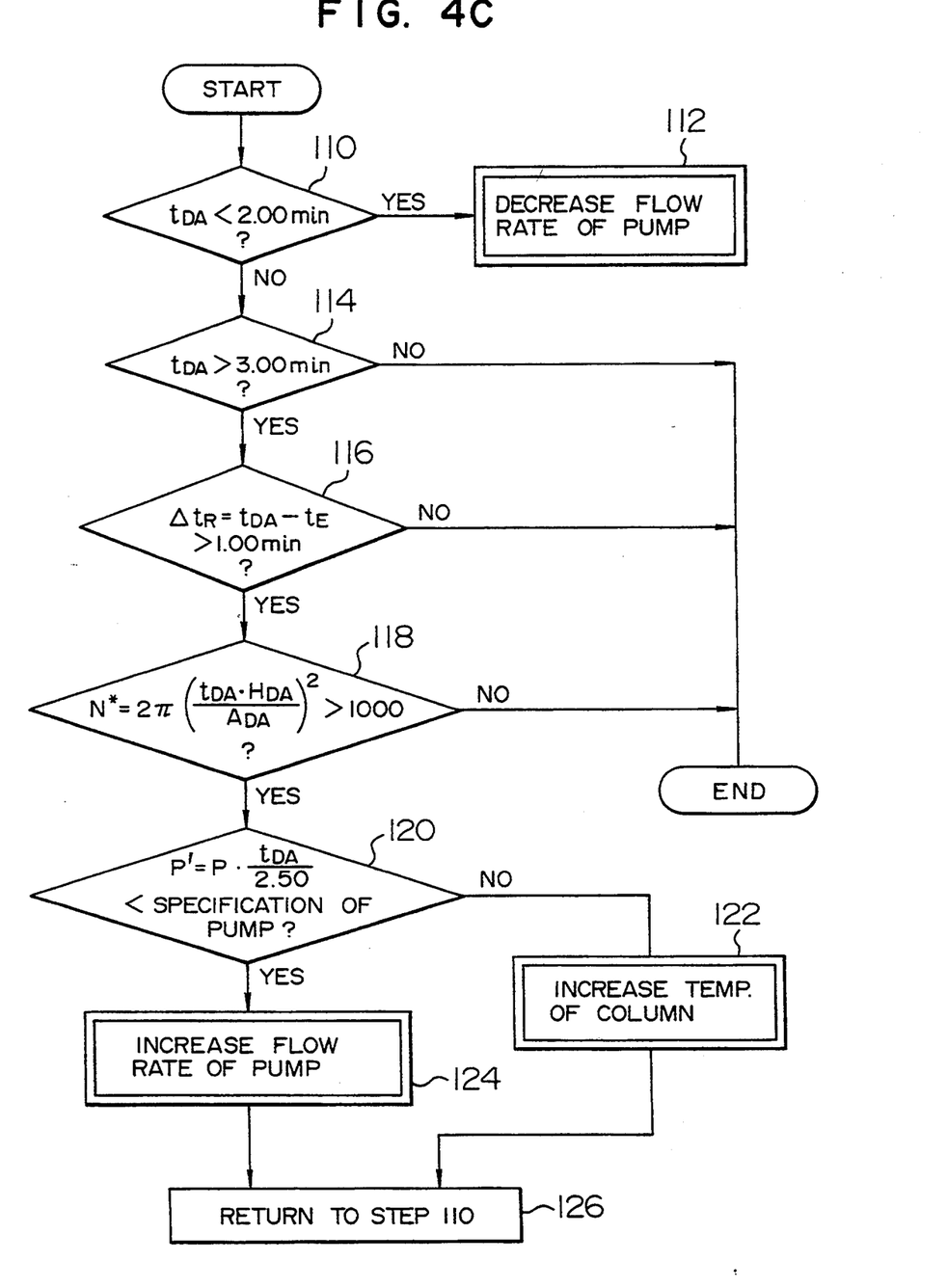
FIG. 4C is another flow-chart showing another method of controlling measurement conditions.

Furthermore, temperature of the column 3 and flow rate of the pump 1 can be controlled according to the retention time $t_{DA}$ of last peak DA. FIG. 4C shows an embodiment thereof. In this embodiment, the last retention time $t_{DA}$ and tolerance thereof are considered to be 2.50 min., and ±0.50 min. respectively, in a normal condition.

If the last retention time $t_{DA}$ is less than 2.00 min., (step 110) the flow rate of pump 1 should be decreased (step 112). The flow rate of pump 1 is controlled by section 6. Specifically, the pressure of pump 1 is decreased so that the current flow rate F decreases to $F(t_{DA}/2.50)$.

If the last retention time $t_{DA}$ is more than 3.00 min. (step 114), an interval $\Delta t_R$ between the peaks DA and E (step 116) and an index of number of a theoretical plates (step 118) are judged. In steps 116 and 118, $t_E$ denotes retention time (min.) of peak E, $H_{DA}$ denotes height (μV) of peak DA and $A_{DA}$ denotes area (μV•min.) of peak DA.

If the interval $\Delta t_R$ is more than 1.00 min. and the index is also more than 1,000, step 120 is performed. In the other cases, the present algorithm finishes and an unknown sample is introduced into the flow line system because the last retention time $t_{DA}$ is considered within the tolerance.

In step 120, the current pressure of the pump 1 is compared with the specification pressure thereof to determine the margin therebetween. Namely, based on the assumption that the pressure of the pump is proportional to the flow rate, the pressure should be inversely proportional to the last retention time $t_{DA}$. Based on this assumption the pressure P' of the pump which renders the last retention time $t_{DA}$ 2.50 min., is calculated, and it is judged whether it the pressure P' is within the specification pressure of the pump, e.g. 100 bar. In the case where the pressure P' is out of the specification, the temperature of column is increased (by 2° K.) to shorten the retention time (step 122). In the case where the pressure P' is within the specification, the pressure of the pump is increased to increase the current flow rate F to F•$(t_{DA}/2.50)$ (step 124).

The above-described correction for the measurement condition is repeated until the last retention time $t_{DA}$ is within the tolerance (step 126).

Moreover, if for the purpose of analyzing blood plasma and urine, standard samples having different concentrations, or standard samples having different concentration ratios are prepared, the analytic condition decision section 14 performs the judgement on the basis of the threshold of the peak area or the area ratio of the three constituents. Thus, it is possible to recognize what is to be analyzed, without any input by the analyst. The section 14 can set the recognized analytic method in the control section 6.

The present embodiment has been described based on the assumption that the catecholamine has the three constituents of NE, E and DA. However, the analysis may be also performed with respect to the specific case where the catecholamine has six constituents including DOPA, DOPAC and DOPEG in addition thereto. In this case, it is possible to select the analytic condition in which the three constituent analysis can be completed in a shorter time than that of the six constituent analysis. The analyzer shown in FIG. 1 can determine the analysis method merely by selecting either the standard sample of three constituents or that of six constituents without an input operation by the operator. During the setup operation of the chromatograph system, the standard sample is measured and the plural peak identification method by the above-mentioned single window is applied. The analytic condition decision section 14 counts the number of peaks having areas exceeding the reference threshold. Then, if the number of peaks is three, the section 14 orders the mechanism control section 6 to carry out the three constituent analysis, while if the number thereof is six, the section 14 orders the section 6 to carry out the six constituent analysis. Thereafter, the analysis proceeds to the standard sample and then to the unknown samples. Moreover, even if no measurement is performed during the setup operation, a procedure can be adopted wherein the standard sample is measured by the six constituent analysis method having a long analysis time, and upon detection of three peaks, the analysis method is switched over to the three constituent analysis method.

Figure 5:
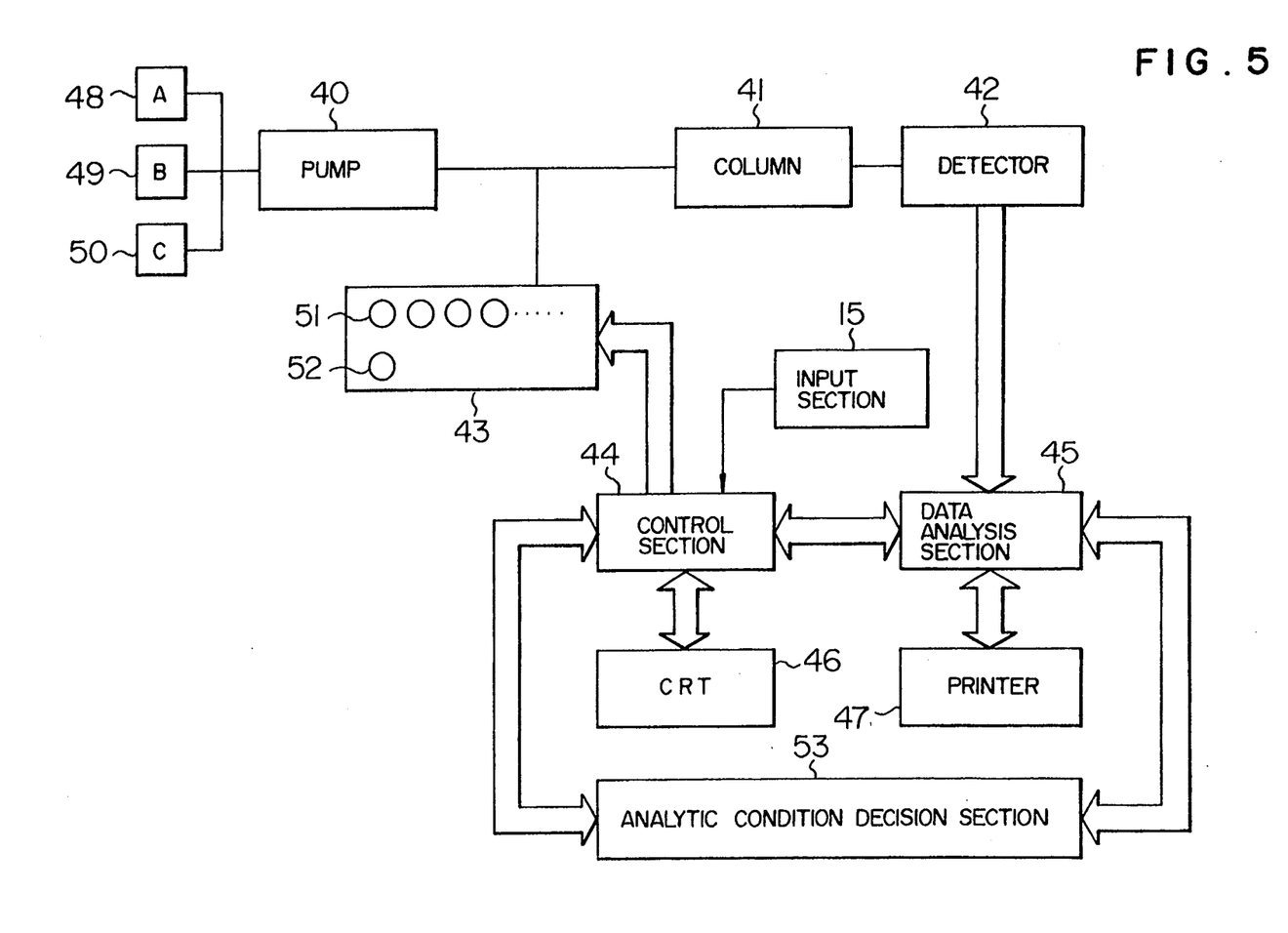
FIG. 5 is a block diagram showing a system arrangement of a glycated hemoglobin analyzer as a second embodiment of the present invention.

Another embodiment of the present invention will hereinafter be described with reference to FIG. 5 and FIG. 6. The system shown in FIG. 5 is a liquid chromatograph analyzer which analyzes glycated hemoglobin by ion exchange chromatography. An eluent feeding pump 40 feeds the eluents A 48, B 49 and C 50 in such a way that A 48, B 49 and C 50 are switched in order to be fed by 1.9 min, 1.0 min and 0.4 min, respectively, for each sample. Thus, the pump 40 performs stepwise elution. Accordingly, with each unnkown sample 51, the stepwise elution is successively performed with a cycle of 3.3 min.

Prior to the chromatography separation of unnkown samples 51, an autosampler 43 having a movable pipetting nozzle sucks 5 μl of a standard sample 52 of hemoglobin (Hb) containing a plurality of constituents to be detected to subject it to dilution treatment, and thereafter feeds the resultant liquid solution to the chromatograph flow line system having a separation column 41. The standard sample is introduced together with the eluent A 48 into the separation column 41 so that the constituents contained therein are separated and spreaded. Each constituent which has been eluted from the separation column 41 is detected by a visible absorbance detector 42. The chromatogram as the detected data is stored in a data analysis section 45.

A signal processing unit including the data analysis section 45 and an analytic condition decision section 53 obtains the peaks corresponding to the constituents to be detected on the basis of the chromatogram of the standard sample, sets the widths of the time windows of the peaks and applies the time windows thus set to the chromatogram of each unknown sample, thereby to identify the constituents contained in each unknown sample. A mechanism control section 44 actuates the sampler 43 when the operation start signal is provided from an input section 15 to make the sampler 43 perform the sampling of the standard sample 52. After the time windows have been set, the section 44 again actuates the sampler 43 to make the sampler 43 perform the sampling of each unknown sample 51. The chromatograms of the standard sample and the unknown samples are outputted to a printer 47 and a CRT 46.

The description will hereinbelow be given to the method of identifying the peaks of the constituents utilizing the chromatogram of the standard sample will be described below referring to FIG. 6. The data analysis section 45 selects the peaks, having areas which are more than or equal to 3,000 $\mu V \bullet s$ from the chromatogram 60 of the standard sample obtained from the detector 42 and applies the time windows shown in Table 4 thereto. As a result, it is recognized that the retention time of the peak Ao is 2.50 min, the retention time of the peak Alc is 1.66 min. The value that of the peak Ala is 0.41 min t shown in Table 4 is the retention time of the measured peak Alc. The peaks L•Alc, F and Alb are calculated on the basis of the expression in Table 4. That is, the peak L•Alc is calculated using (1.46±0.15) min expressed by the calculation result of (1.00×1.66−0.20) and the tolerance therefor as the time window. In FIG. 6, the corresponding peak is not identified. In a similar manner, the time window of the peak F is calculated to be in the range of (0.97±0.15) min, and that of the peak Alb is calculated to be in the range of (0.56±0.20) min. In the case of FIG. 6, the retention time of the peak F is 0.97 min and that of the peak Alb is 0.64 min.

TABLE 4

|   | Retention time (min) | ± Tolerance (min) |
|---|---|---|
| Ala | 0.30 | 0.15 |
| Alb | 0.30t + 0.06 | 0.20 |
| F | 0.65t − 0.11 | 0.15 |
| L · Alc | 1.00t − 0.20 | 0.15 |
| Alc | 1.60 | 0.40 |
| Ao | 2.60 | 0.30 |

The individual time windows which are reduced with respect to the peaks Ao and Alc are applied to the chromatograms of the unknown samples 51. That is, the time window for the peak Ao is set to (2.50±0.15) min and the time window for the peak Alc is set to (1.66±0.15) min.

The peak L•Alc or F as the sub-peak may not be separated and detected from the Hb standard sample 52 in some cases. Therefore, the above-mentioned method is available. The data analysis section 45 performs the identification with respect to the chromatogram in accordance with the procedure described above. First, the peaks having areas exceeding the threshold are selected. Subsequently, Ao and Alc are identified using the above-mentioned reduced time window method. The analytic condition decision section 53 reduces the tolerances of the peaks Ao and Alc to ±0.15 for the unknown sample 51 of the blood. Then, the time window of each remaining peak is calculated on the basis of the retention time of Alc and the data analysis section 45 performs the identification.

Figure 7:
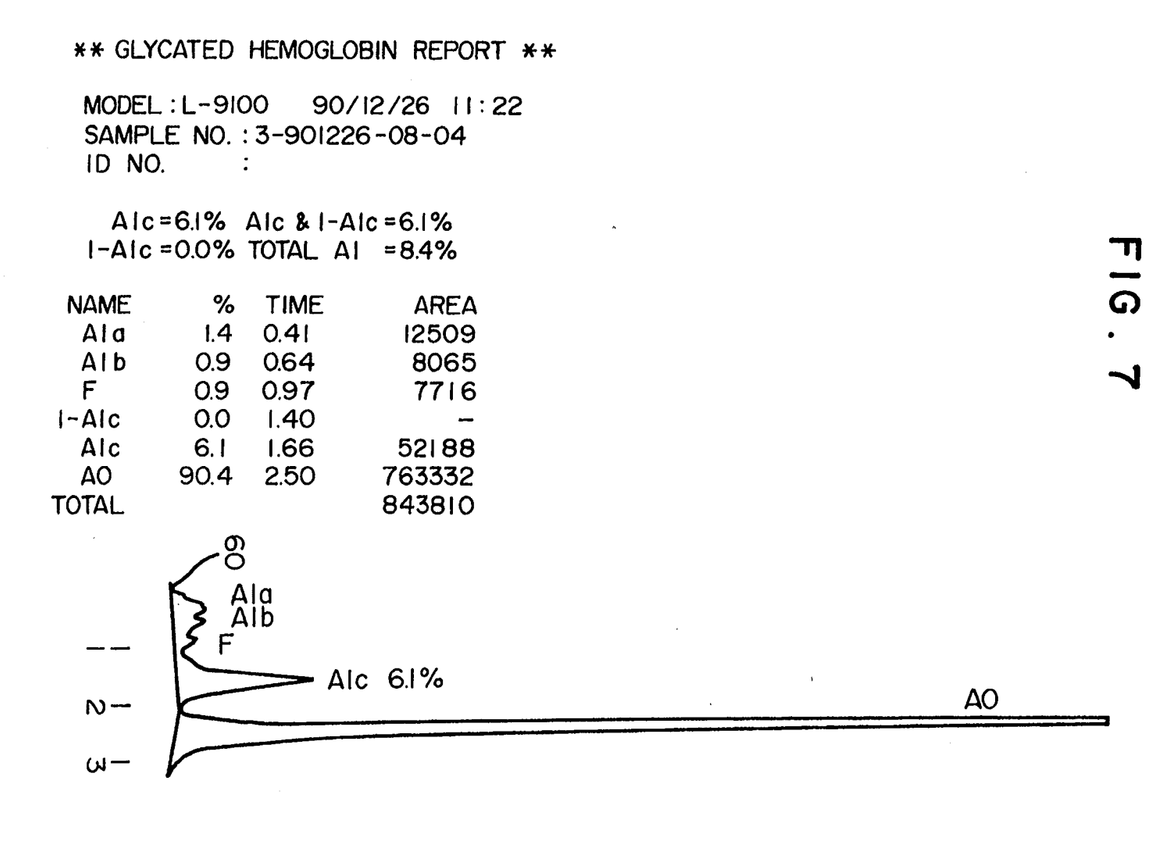
FIG. 7 is a view showing an example of a chromatogram obtained by the system of FIG. 5.

The time window of each peak is a function inherent in the retention time of Alc. This can be regarded as the developed identification method due to the relative retention time in which the retention time of the sub-peak is proportional to the retention time of the main peak. In other words, in this case, the proportional calculation is extended to the general function, and the time windows are used as the functions inherent in the associated peaks. This method is usable in chromatography employing the elution method in which the proportional relationship is not simply established among the retention times. The peaks L•Alc, F, Alb and Ala are identified in the order of decreasing retention time. With the determination value of each constituent, the ratio formed by the peak area thereof is displayed in the form of a percentage on the CRT 46 through the control section 44. Moreover, the identified chromatogram is printed as shown in FIG. 7 by the printer 47. If no peak is present in the calculated time window, the searched time is printed and the determination value becomes 0.0%. Thereafter, when the unknown samples 51 are analyzed, Ao and Alc are identified using the reduced time window method, while the peaks L•Alc, F, Alb and Ala are identified using the respective variable time window method.

FIG. 7 shows the observed data thus obtained.

Still another peak identification method will now be described. To this identification method is applied a method of identifying the peaks of plural constituents to be detected which are obtained by the chromatography separation using the above-mentioned single time window.

In this identification method, the constituents of the standard sample are first separated by the separation column and then the peaks having areas which are more than or equal to 3,000 $\mu V \bullet s$ are selected. Next, using the time windows of Table 5, the peaks having vertexes present in the associated time window are detected.

Subsequently, with the time window A of Table 5, two peaks are selected in the order of decreasing area. In this case, (1) if all of the two peaks are selected, the peaks are identified as Ala and Alb in the order of increasing retention time, and (2) if only one peak is selected, the peak is identified as Alb.

TABLE 5

| Time Window | (min) |
|---|---|
| A | 0.0–1.0 |
| B | 1.1–2.3 |
| C | 2.4–3.0 |

Next, with the time window B of Table 5, three peaks are selected in the order of decreasing area. In this case, (1) if all of the three peaks are selected, the peaks are identified as F, L•Alc and Alc in the order of increasing retention time, and (2) if two peaks are selected, the peak having a larger retention time is identified as Alc. Another peak is identified as L•Alc if its retention time is within 0.4 min. of Alc Otherwise, it is identified as F. (3) If only one peak is selected, it is identified as Alc.

Further, with the time window C of Table 5, the peak having the largest area is identified as Ao.

Figure 6:
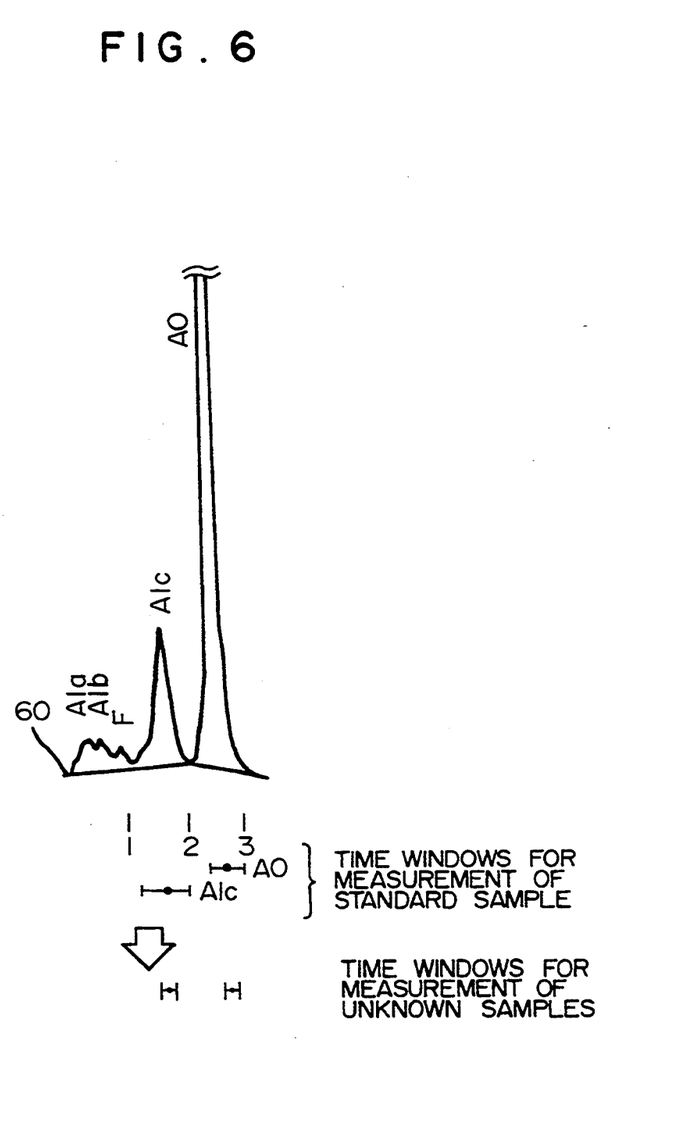
FIG. 6 is a view useful in explaining a peak identification method employed in the system of FIG. 5.

In order to carry out this identification method, first, the data analysis section 45 of FIG. 5 detects the peaks having areas which are more than or equal to 3,000

μV•s from the chromatogram 60 as shown in FIG. 6. Then, the chromatogram 60 is divided into three time windows. With each time window, the peaks each having a large area are selected and then are identified in accordance with the rules. The analytic condition decision section 53 receives the identification result. Then, if Ao and A1c are not identified, the identification result is judged to be an error. If Ao and A1c are identified, the section 53 orders the control section 44 to proceed to the analysis of the subsequent unknown sample 51.

In the glycated hemoglobin analyzer, in the same manner as in the catecholamine analyzer, the retention times of the individual peaks may deviate from the reference value. In such a case, the pump flow rate and column temperature may be changed as described above. Moreover, since the glycated hemoglobin analyzer performs the stepwise elution, the analytic condition decision section 53 may perform the calculation in accordance with the rules to order the control section 44 to change the switching time of each eluent. In this case, the control section 44 changes the conditions of the control and again measures the standard sample.

As set forth hereinabove, according to the present invention, the operator of the analyzer only sets the samples to start the operation and the analytic conditions are automatically determined by the analyzer itself. Therefore, the operator of the analyzer is freed from the necessity of examining the analytic conditions.

We claim:

1. A method of performing a chromatography analysis of an unknown sample, the method comprising the steps of:
   (a) performing chromatography analysis of a standard sample to obtain a chromatogram of the standard sample, the standard sample including constituents to be measured in the unknown sample;
   (b) defining first retention time windows within which peaks corresponding to the constituents to be measured are expected to appear in the chromatogram of the standard sample, the first retention time windows being defined by first retention times and first tolerances about the first retention times;
   (c) detecting peaks in the chromatogram of the standard sample appearing within the first retention time windows;
   (d) determining at least one of (1) whether or not areas of the detected peaks conform with predetermined areas indicative of the peaks corresponding to the constituents to be measured and (2) whether or not heights of the detected peaks conform with predetermined heights indicative of the peaks corresponding to the constituents to be measured;
   (e) defining second retention time windows corresponding to the constituents to be measured only if it is determined that at least one of (1) the areas of the detected peaks conform with the predetermined areas indicative of the peaks corresponding to the constituents to be measured and (2) the heights of the detected peaks conform with the predetermined heights indicative of the peaks corresponding to the constituents to be measured, the second retention time windows being defined by second retention times and second tolerances about the second retention times, the second retention times being equal to retention times of the detected peaks, the second tolerances being smaller than the first tolerances;
   (f) performing chromatography analysis of the unknown sample to obtain a chromatogram of the unknown sample; and
   (g) identifying in the unknown sample the constituents to be measured by analyzing the chromatogram of the unknown sample using the second retention time windows.

2. A method according to claim 1, wherein the first retention time windows are different from each other.

3. A method according to claim 1, wherein the steps (b) through (e) are automatically performed by an apparatus without participation by a human operator performing the chromatography analysis.

4. A method of performing a chromatography analysis of an unknown sample, the method comprising the steps of:
   (a) performing chromatography analysis of a standard sample to obtain a chromatogram of the standard sample, the standard sample including constituents to be measured in the unknown sample;
   (b) defining a first retention time window within which peaks corresponding to the constituents to be measured are expected to appear in the chromatogram of the standard sample, the first retention time window being defined by a first retention time and a first tolerance about the first retention time;
   (c) detecting peaks in the chromatogram of the standard sample appearing within the first retention time window;
   (d) determining (1) whether or not the detected peaks are equal in number to the constituents to be measured and (2) whether or not areas of the detected peaks are at least equal to a predetermined area, the predetermined area being greater than zero;
   (e) determining at least one of (1) whether or not areas of the detected peaks conform with predetermined areas indicative of the peaks corresponding to the constituents to be measured and (2) whether or not heights of the detected peaks conform with predetermined heights indicative of the peaks corresponding to the constituents to be measured only if it is determined that (1) the detected peaks are equal in number to the constituents to be measured and (2) the areas of the detected peaks are at least equal to the predetermined area;
   (f) defining second retention time windows corresponding to the constituents to be measured only if it is determined that at least one of (1) the areas of the detected peaks conform with the predetermined areas indicative of the peaks corresponding to the constituents to be measured and (2) the heights of the detected peaks conform with the predetermined heights indicative of the peaks corresponding to the constituents to be measured, the second retention time windows being defined by second retention times and second tolerances about the second retention times, the second retention times being equal to the retention times of the detected peaks, the second tolerances being smaller than the first tolerance;
   (g) performing chromatography analysis of the unknown sample to obtain a chromatogram of the unknown sample; and
   (h) identifying in the unknown sample the constituents to be measured by analyzing the chromatogram of the unknown sample using the second retention time windows.

5. A method according to claim 4, wherein the steps (b) through (f) are automatically performed by an apparatus without participation by a human operator performing the chromatography analysis.

6. An apparatus for performing a chromatography analysis of an unknown sample, the apparatus comprising:
   (a) means for performing chromatography analysis of a standard sample to obtain a chromatogram of the standard sample, the standard sample including constituents to be measured in the unknown sample;
   (b) means for defining first retention time windows within which peaks corresponding to the constituents to be measured are expected to appear in the chromatogram of the standard sample, the first retention time windows being defined by first retention times and first tolerances about the first retention times;
   (c) means for detecting peaks in the chromatogram of the standard sample appearing within the first retention time windows;
   (d) means for determining at least one of (1) whether or not areas of the detected peaks conform with predetermined areas indicative of the peaks corresponding to the constituents to be measured and (2) whether or not heights of the detected peaks conform with predetermined heights indicative of the peaks corresponding to the constituents to be measured;
   (e) means for defining second retention time windows corresponding to the constituents to be measured only if it is determined that at least one of (1) the areas of the detected peaks conform with the predetermined areas indicative of the peaks corresponding to the constituents to be measured and (2) the heights of the detected peaks conform with the predetermined heights indicative of the peaks corresponding to the constituents to be measured, the second retention time windows being defined by second retention times and second tolerances about the second retention times, the second retention times being equal to retention times of the detected peaks, the second tolerances being smaller than the first tolerances;
   (f) means for performing chromatography analysis of the unknown sample to obtain a chromatogram of the unknown sample; and
   (g) means for identifying in the unknown sample the constituents to be measured by analyzing the chromatogram of the unknown sample using the second retention time windows.

7. An apparatus according to claim 6, wherein the first retention time windows are different from each other.

8. An apparatus according to claim 6, wherein the means (b) through (e) operate automatically without participation by a human operator operating the apparatus.

9. An apparatus for performing a chromatography analysis of an unknown sample, the apparatus comprising:
   (a) means for performing chromatography analysis of a standard sample to obtain a chromatogram of the standard sample, the standard sample including constituents to be measured in the unknown sample;
   (b) means for defining a first retention time window within which peaks corresponding to the constituents to be measured are expected to appear in the chromatogram of the standard sample, the first retention time window being defined by a first retention time and a first tolerance about the first retention time;
   (c) means for detecting peaks in the chromatogram of the standard sample appearing within the first retention time window;
   (d) means for determining (1) whether or not the detected peaks are equal in number to the constituents to be measured and (2) whether or not areas of the detected peaks are at least equal to a predetermined area, the predetermined area being greater than zero;
   (e) means for determining at least one of (1) whether or not areas of the detected peaks conform with predetermined areas indicative of the peaks corresponding to the constituents to be measured and (2) whether or not heights of the detected peaks conform with predetermined heights indicative of the peaks corresponding to the constituents to be measured only if it is determined that (1) the detected peaks are equal in number to the constituents to be measured and (2) the areas of the detected peaks are at least equal to the predetermined area;
   (f) means for defining second retention time windows corresponding to the constituents to be measured only if it is determined that at least one of (1) the areas of the detected peaks conform with the predetermined areas indicative of the peaks corresponding to the constituents to be measured and (2) the heights of the detected peaks conform with the predetermined heights indicative of the peaks corresponding to the constituents to be measured, the second retention time windows being defined by second retention times and second tolerances about the second retention times, the second retention times being equal to the retention times of the detected peaks, the second tolerances being smaller than the first tolerance;
   (g) means for performing chromatography analysis of the unknown sample to obtain a chromatogram of the unknown sample; and
   (h) means for identifying in the unknown sample the constituents to be measured by analyzing the chromatogram of the unknown sample using the second retention time windows.

10. An apparatus according to claim 9, wherein the means (b) through (f) operate automatically without participation by a human operator operating the apparatus.

* * * * *